United States Patent
Sharma et al.

(10) Patent No.: US 6,816,248 B2
(45) Date of Patent: Nov. 9, 2004

(54) HAND-HELD AUTOMATIC REFRACTOMETER

(75) Inventors: Keshav D. Sharma, Lancaster, NY (US); Kyle R. Bleyle, Lancaster, NY (US)

(73) Assignee: Reichert, Inc., Depew, NY (US)

( * ) Notice: Subject to any disclaimer, the term of this patent is extended or adjusted under 35 U.S.C. 154(b) by 608 days.

(21) Appl. No.: 09/842,463

(22) Filed: Apr. 26, 2001

(65) Prior Publication Data

US 2002/0159050 A1 Oct. 31, 2002

(51) Int. Cl.⁷ .............................................. G01N 21/41
(52) U.S. Cl. ...................................................... 356/136
(58) Field of Search ............................... 356/128–137; 250/227.11–227.14, 269.1

(56) References Cited

U.S. PATENT DOCUMENTS

| | | | |
|---|---|---|---|
| 4,640,616 A | 2/1987 | Michalik | 356/136 |
| 6,097,479 A * | 8/2000 | Melendez et al. | 356/136 |
| 6,172,746 B1 | 1/2001 | Byrne et al. | 356/135 |

* cited by examiner

Primary Examiner—Tu T. Nguyen
(74) Attorney, Agent, or Firm—Hodgson Russ LLP

(57) ABSTRACT

A hand-held automatic refractometer comprises a linear scanned array having a plurality of photoelectric cells and an optical system for directing light onto the array, the particular photoelectric cells of the array which are illuminated by said light being determined by the index of refraction of a sample substance placed on a sample surface of a prism of the optical system. A reflective surface is arranged close to the array at an acute angle thereto for directing primary light from the sample-prism boundary to the array, and for redirecting stray reflected light from the array back onto the array. The disclosed refractometer has a compact design wherein the linear array extends in a direction substantially parallel to the prism sample surface. The prism is mounted in a housing and the sample surface faces upward to allow access through a sample well of the housing, while the array is mounted in the housing facing in a downward direction.

11 Claims, 5 Drawing Sheets

HAND-HELD AUTOMATIC REFRACTOMETER

BACKGROUND OF THE INVENTION

The present invention relates generally to refractometers for measuring refractive index of a substance, and more particular to an automatic refractometer of compact design for easy hand-held operation.

Refractometers measure the critical angle of total reflection by directing an obliquely incident non-collimated beam of light at a surface-to-surface boundary between a high refractive index prism and the sample to allow a portion of the light to be observed after interaction at the boundary. In transmitted light refractometers, light that is transmitted through the sample and prism is observed, while in reflected light refractometers, the light that is reflected due to total reflection at the surface-to-surface boundary is observed. In either case, an illuminated region is produced over a portion of a detection field of view, and the location of the shadowline between the illuminated region and an adjacent dark region in the detection field of view allows the sample refractive index to be deduced geometrically.

In simpler hand-held refractometers used in industry, a reticle scale is superimposed in the field of view and the operator looks through an eyepiece to observe the location of the shadowline with respect to the reticle scale, which is marked so as to provide desired information such as percentage concentration of solids in the sample. Illumination of the test sample can be provided by ambient illumination, or by a dedicated light source near the sample as disclosed for instance by U.S. Pat. No. 4,650,323. Hand-held refractometers are desirable because they enable periodic on-site measurements to be performed on substances as a means of quality assurance. Since the refractive index of a liquid substance is related to the concentration of elements within the substance, hand-held refractometers are used widely in the soft drink industry to monitor sugar concentration and in the machine tool industry to check the lubricant concentration in cutting fluid. As a further example, U.S. Pat. No. 6,034,762 describes a hand-held refractometer for measuring the water content in hydraulic fluids such as brake fluid. The measurement results of hand-held refractometers have limited accuracy (closeness to the true value) and precision (repeatability regardless of accuracy) due to the fact that an operator judges the shadowline location with respect to a reticle scale, thereby introducing an element of human error into each reading.

The desire for greater accuracy and precision has led to the development of automatic refractometers that remove the guesswork associated with visually determining shadowline location with respect to a reticle scale. U.S. Pat. No. 4,640,616 (Michalik) and U.S. Pat. No. 6,172,746 (Byrne et al.) disclose automatic refractometers wherein a linear scanned array (LSA) of photosensitive elements or "cells" is arranged to detect light after interaction at a sample/prism boundary. In commercial embodiments, the linear scanned array includes a straight line of charge-coupled device (CCD) cells that are scanned electronically to provide a series of pulse signals each having an amplitude proportional to the amount of illumination received by the cell from incident light. Light received by the linear scanned array divides the array into an illuminated region and an adjacent dark region, thereby forming a shadowline on the array. The particular cell or interpolated inter-cell fraction at which the shadowline crosses the linear scanned array is determined by the index of refraction of the sample substance placed in contact with the prism. The output from the photoelectric cells is digitized and processed to find the cell location where the transition shadowline crosses the array, from which the refractive index and concentration of interest can be calculated. Automatic refractometers of the prior art are larger and heavier than their hand-held counterparts, and include optical means designed to provide sufficient light flux initially reaching the detector array to achieve a favorable signal-to-noise ratio with respect to the detector array. In these instruments, compactness in the arrangement of the optical elements is not a limiting design factor.

SUMMARY OF THE INVENTION

Therefore, it is an object of the present invention to provide an automatic refractometer that is compact and lightweight for hand-held use.

It is another object of the present invention to provide a hand-held automatic refractometer that provides highly accurate and precise measurement readings.

It is yet another object of the present invention to provide a hand-held automatic refractometer with an optical system that maximizes the use of illumination from a light source to provide a desirable signal-to-noise ratio at a photosensitive array of the refractometer without relying on increased power consumption by the light source.

It is yet another object of the present invention to provide a hand-held automatic refractometer with a physically compact optical system that results in an illumination distribution at a photosensitive array of the refractometer that is free of anomalies that might affect measurement readings.

In furtherance of these and other objects, a hand-held automatic refractometer of the present invention generally comprises a linear scanned array having a plurality of photoelectric cells, and optical means for directing light onto the array such that the particular photoelectric cells of the array which are illuminated by the light are determined by the index of refraction of a sample substance placed in operative association with the optical means, wherein the optical means acts also to receive stray light reflected by the array and redirect the light back onto the array. More specifically, the optical means includes a prism having a sample-receiving surface for establishing a critical angle boundary, a source of non-parallel light obliquely directed at the sample-prism boundary, and a reflective surface positioned proximate the linear scanned array at an acute angle relative thereto. The reflective surface is orientated to perform two functions. First, the reflective surface receives light internally reflected at the sample prism boundary and directs the light toward the linear scanned array. Second, the reflective surface receives a small amount of light that is reflected by the linear scanned array and redirects the light back upon the array. In a preferred embodiment, the reflective surface is made long enough such that a portion of the reflective surface receives none of the initial light flux, but rather is dedicated strictly to returning secondary reflected light from the array back onto the array. Also according to a preferred embodiment, the linear scanned array is arranged to extend in a direction that is parallel to or substantially parallel to the sample-receiving surface for a low-profile design, with the sample surface facing upward and the array facing downward.

The refractometer further comprises signal processing electronics and a display for converting the output from the linear scanned array to a meaningful measurement result and reporting the result.

BRIEF DESCRIPTION OF THE SEVERAL VIEWS OF THE DRAWINGS

The nature and mode of operation of the present invention will now be more fully described in the following detailed description of the invention taken with the accompanying drawing figures, in which.

DETAILED DESCRIPTION OF THE INVENTION

Figure 1:
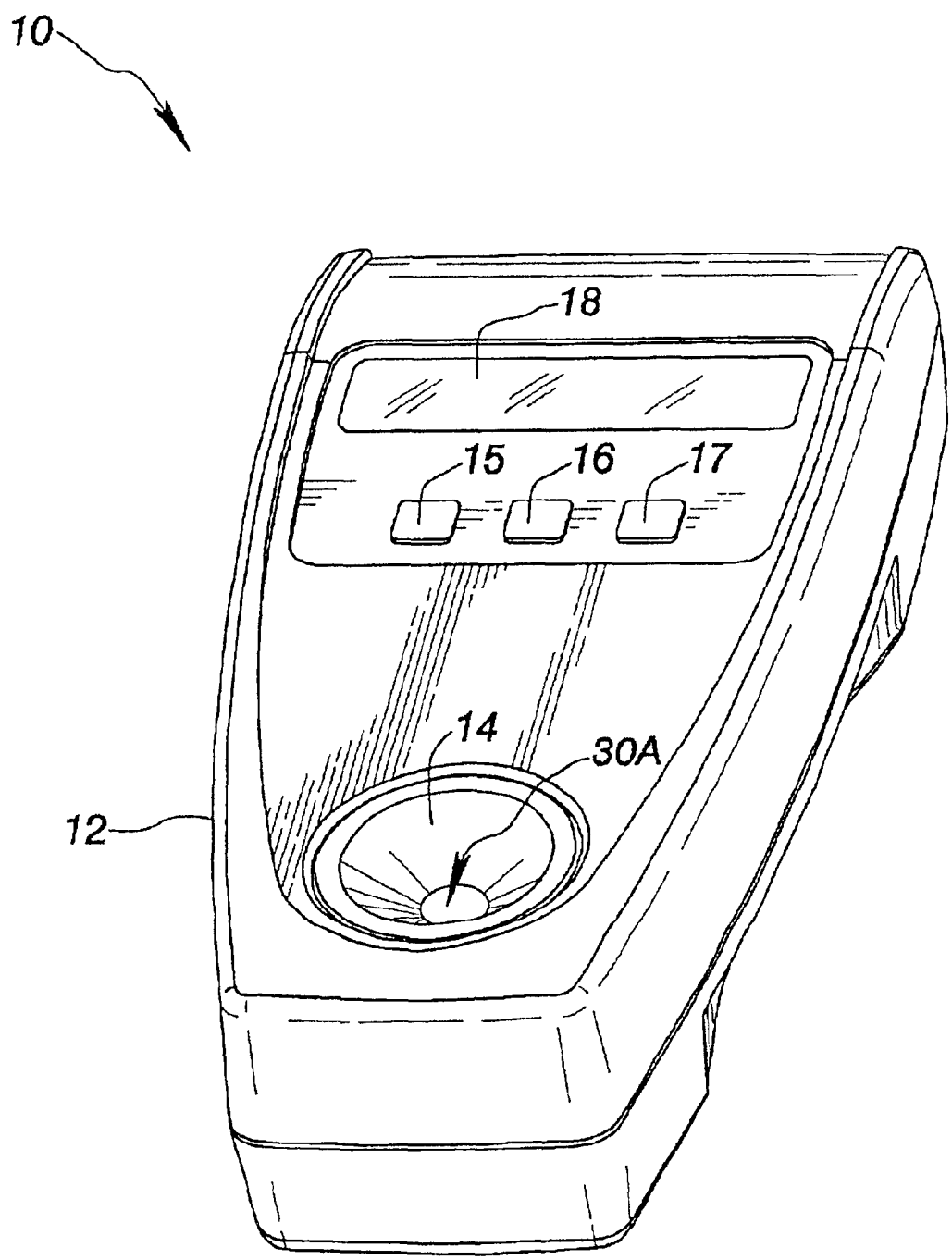
FIG. 1 is a perspective view of a hand-held automatic refractometer formed in accordance with a preferred embodiment of the present invention.

Referring initially to FIG. 1, an automatic hand-held refractometer formed in accordance with a preferred embodiment of the present invention is shown and broadly designated by the reference numeral 10. Refractometer 10 generally comprises a housing 12, a frustoconical sample well 14 mounted in a front portion of housing 12, a calibration control button 15, a read control button 16, a mode control button 17, and an LCD display panel 18.

Figure 2:
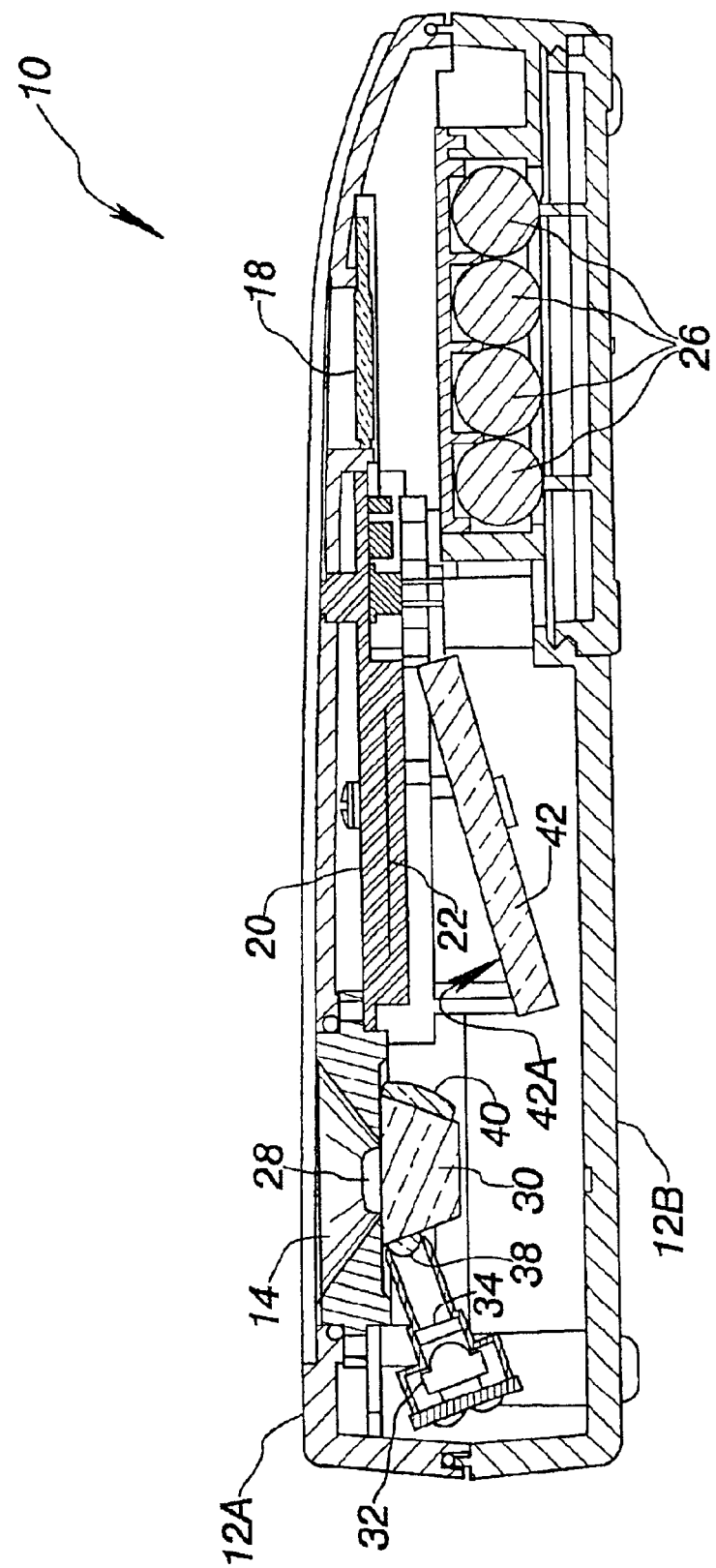
FIG. 2 is a cross-sectional view of the hand-held automatic refractometer shown-in FIG. 1.

Attention is directed also now to the cross-sectional view of FIG. 2. Housing 12 contains a main circuit board 20 on which a linear scanned array 22 is mounted, optical means 24 for directing light onto linear scanned array 22 as will be described in detail below, and a power source in the form of batteries 26. Housing 12 is manufactured to have a top portion 12A and a bottom portion 12B for assembly purposes, and is sized to be a compact unit that is easily held in the hand of an operator.

Figure 3:
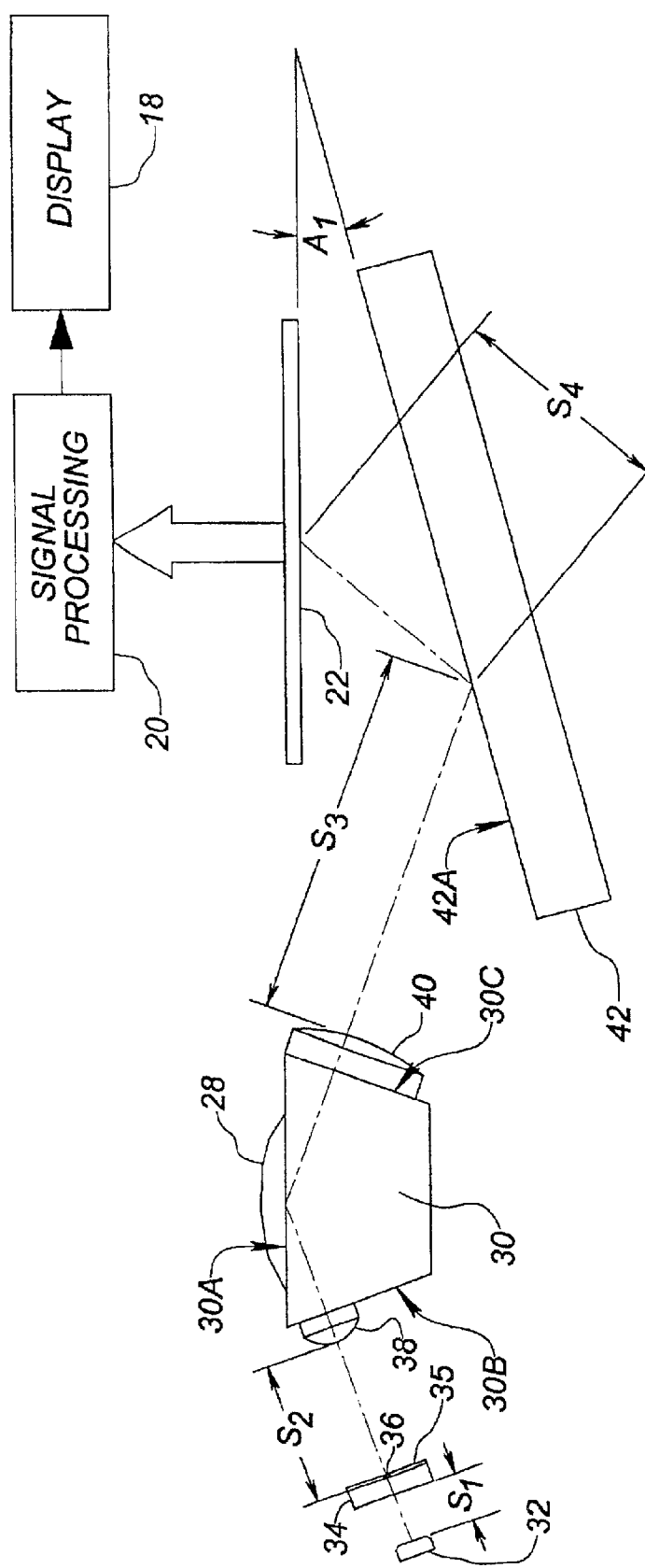
FIG. 3 is a schematic diagram showing an optical system of the hand-held automatic refractometer in detail.
Figure 4A:
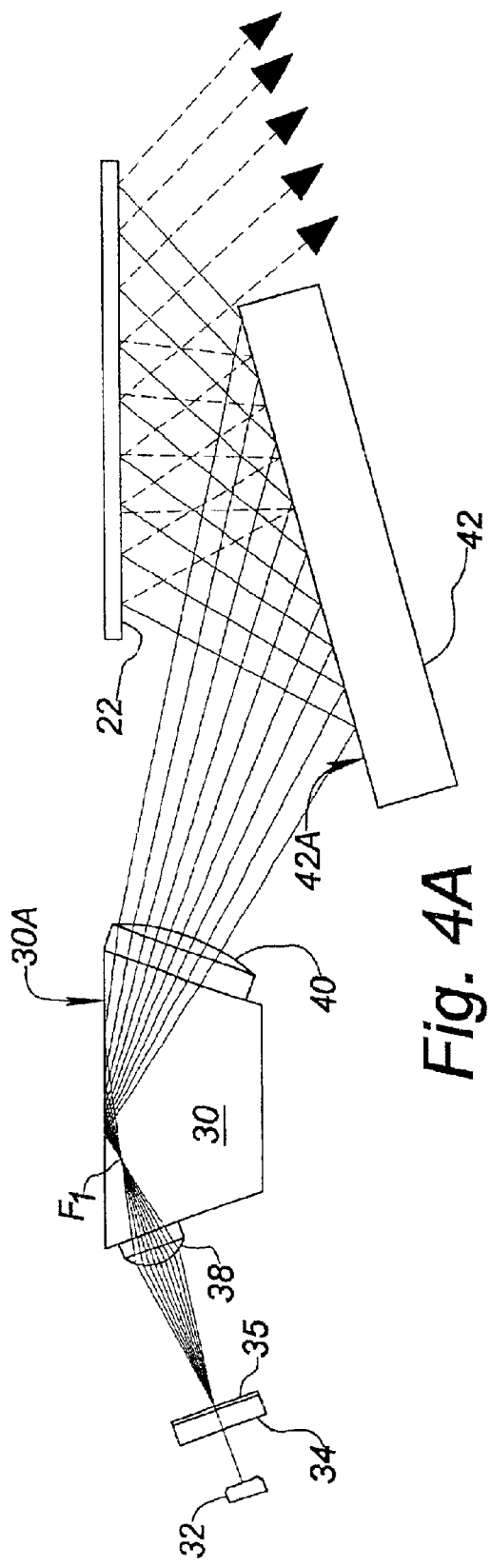
FIG. 4A is an optical schematic diagram similar to that of FIG. 3 showing ray traces with air as a reference sample and a short mirror for directing light onto a detector array of the optical system.
Figure 4B:
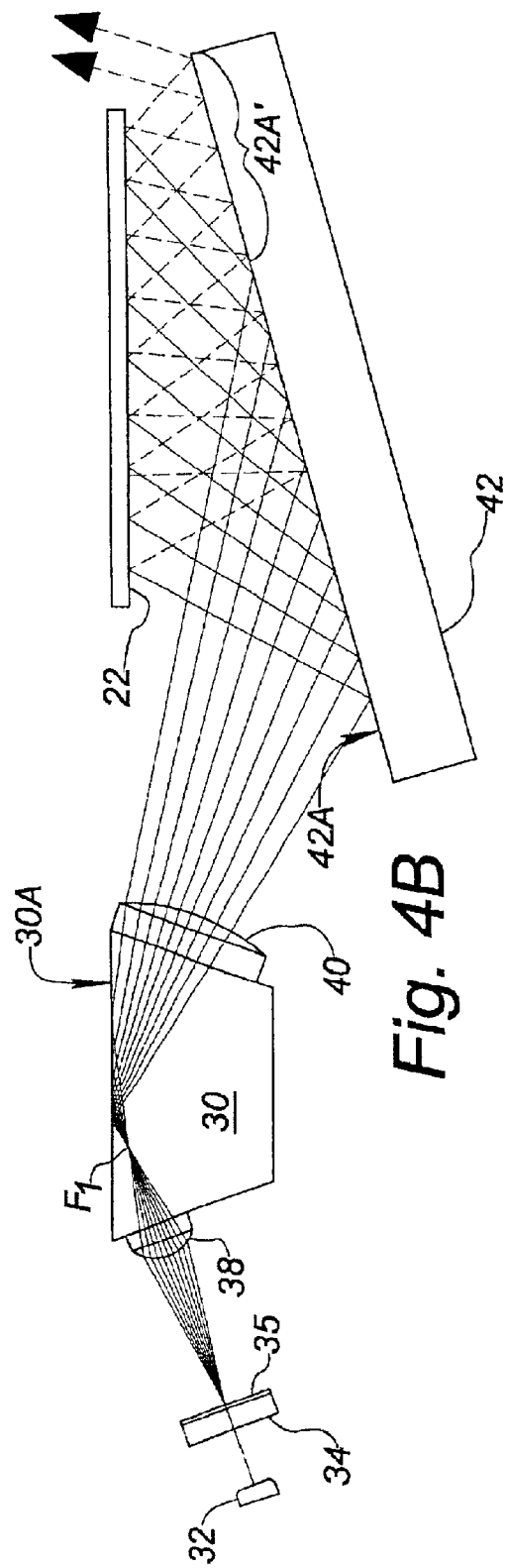
FIG. 4B is an optical schematic diagram similar to that of FIG. 4A, however showing the use of a longer mirror for directing light onto the detector array.

The optical means 24 of the preferred embodiment comprises a high index prism 30 having an external sample surface 30A for receiving a sample 28 to be tested, as shown in FIG. 3. Referring also to FIGS. 4A and 4B, non-parallel light is obliquely directed to the surface boundary between sample 28 and prism 30 by means of a light emitting diode 32, a diffuser 34 immediately downstream of light emitting diode 32, an occluder 35 having a pinhole aperture 36 through which diffuse light passes, and a first lens 38 cemented to a light entry surface 30B of prism 30 for focusing the light at a point $F_1$ slightly in front of sample surface 30A. The divergent light from point $F_1$ includes rays having an angle of incidence greater than the critical angle of total internal reflection and rays having an angle of incidence not greater than the critical angle of total internal reflection, such that the former rays will be internally reflected at the sample/prism boundary to continue along a path to linear scanned array 22, while the latter rays will be refracted by sample 28 and pass out of the system. The internally reflected light passes successively through an exit surface 30C of prism 30 and a second lens 40 cemented to the exit surface. The light then strikes a reflective surface 42A of a mirror 42 and is thereby redirected toward linear scanned array 22. Those skilled in the art realize that the index of refraction of sample 28 is a variable that determines the critical angle of total internal reflection at the prism-sample boundary, and thus the location of a shadowline between illuminated and dark regions on linear scanned array 22.

By way of non-limiting example, prism 30 is manufactured from Schott SK2 optical glass having a refractive index $n_e$=1.60994 and is 18 mm in length along sample surface 30A, which forms a 70° angle with entry surface 30B and a 70° angle with exit surface 30C; diffuser 34 is 5.5 mm in diameter by 1.5 mm thick and is formed of window glass having one surface ground with a No. 25T size abrasive; first lens 38 is a plano-convex lens of Schott SK2 optical glass that is 3.8 mm in diameter by 2 mm overall thickness, with a 2.3 mm radius of curvature on the convex face; second lens 40 is a plano-convex lens of Schott SK2 optical glass that is 9 mm in diameter by 2.5 mm overall thickness, with a 12 mm radius of curvature on the convex face; and mirror 42 is annealed pyrex polished on reflective surface 42A, which is 44 mm in length as viewed in FIG. 3. Further by way of non-limiting example, linear scanned array 22 is preferably a Toshiba TCD1304AP CCD linear image sensor having 3648 individual photoelectric cells over a length of approximately 29 mm. In accordance with the present example, the following spacing distances are used: $S_1$=3.35 mm, $S_2$=9.24 mm, $S_3$=24.36 mm, and $S_4$=14.54 mm. In the example now described, linear scanned array 22 is orientated such that its cells reside in a plane that is substantially parallel to sample surface 30A of prism 30, and reflective surface 42A of mirror 42 is arranged such that it forms an acute angle A1 with the plane of linear scanned array 22 and is closely proximate to the array, thereby giving the optical system of the present invention a low profile height and short overall length desirable for a compact hand-held refractometer. In the exemplary embodiment shown, angle A1 is equal to 15°.

It is noted that the planar surface of plano-convex lens 38 is fixed in surface-to surface contact with planar entry surface 30B of prism 30 using optical cement, and the planar surface of plano-convex lens 40 is likewise fixed in surface-to surface contact with planar exit surface 30C of prism 30 using optical cement. In this way, separate mounting structure for supporting lenses 38 and 40 and aligning the lenses in the optical system is avoided, and temperature changes experienced by the prism proper are also experienced by the affixed lenses.

Figure 5:
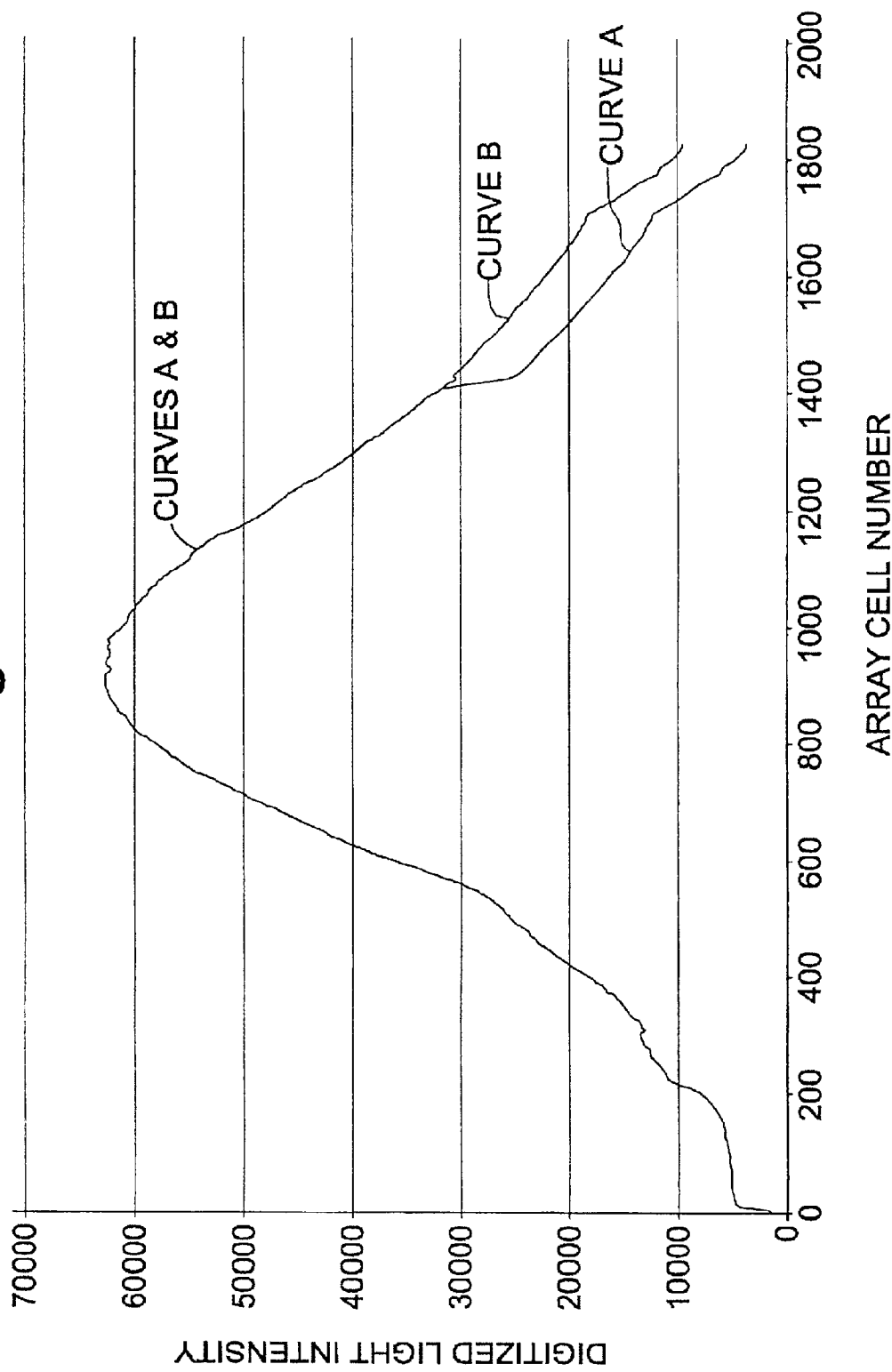
FIG. 5 is a comparative plot of light intensity as a function of cell number for reference scans of a linear scanned array of the refractometer without and with benefit of secondary reflections from the linear scanned array.

As will be appreciated from FIGS. 4A, 4B, and 5, the arrangement of reflective surface 42A at a small acute angle relative to the plane of linear scanned array 22 and closely proximate to the array carries a desirable optical consequence in terms of the illumination distribution incident upon the array. Specifically, a small portion of the light flux incident upon linear scanned array 22 is actually reflected by the array back in the direction of reflective surface 42A, as indicated by broken line rays in FIGS. 4A and 4B. This secondary light is then reflected again by reflective surface 42A either back toward linear scanned array 22 or out of the system. During development of the present invention, it was found that the use of a mirror 42 having a relatively short reflective surface 42A, as depicted in FIG. 4A, resulted in the loss of illumination intensity at a portion of linear scanned array 22 that did not receive any secondary reflected light due to the shortened mirror. The intensity distribution graph of FIG. 5 illustrates this problem by showing a sharp drop-off or shift in intensity in Curve "A" where a shorter reflective surface is used. To counter this problem, and to take advantage of the increased signal-to-noise ratio provided by secondary reflections, reflective surface 42A was extended, as represented by reflective surface portion 42A' shown in FIG. 4B, such that rays previously escaping the system in FIG. 4A are redirected back onto the linear scanned array 22. As will be understood from Curve "B" of FIG. 5, the longer mirror eliminates the problem of intensity drop-off at the affected portion of the intensity distribution curve. It will be appreciated that extended portion 42A' of reflective surface 42A is provided solely for receiving and reflecting secondary light reflected from the surface of array 22, and receives no light directly from lens 40.

As is known in the art of automatic refractometers, the pulse signals from the cells of linear scanned array 22 are digitized and the data are processed by an algorithm designed to determine the location of a shadowline transition between an illuminated region of the array and a dark region of the array. The cell crossing number of the shadowline on linear scanned array 22 is then used to geometrically calculate the index of refraction of the sample substance 28. Various algorithms are available, as taught for example by U.S. Pat. Nos. 4,640,616; 5,617,201; and 6,172,746; and by commonly-owned U.S. patent application Ser. No. 09/794,991 filed Feb. 27, 2001, each of these documents being hereby incorporated by reference in the present specification.

Since the illumination intensity distribution curve will naturally contain a steep transition representing the transition between light and dark regions of the array, the elimination of the unrelated drop-off seen in Curve "A" of FIG. 5 prevents potentially confusing data from being inputted to the algorithm. This allows a simpler algorithm to be used which does not have to distinguish between a drop-off from lack of secondary light and a transition between light and dark regions related to the critical angle of total internal reflection at the prism-sample boundary.

While the preferred embodiment described herein relates to a reflected light refractometer having an internal source of illumination, the invention can also be applied to a transmitted light refractometer and to a refractometer that uses an external illumination source, including ambient illumination.

What is claimed is:

1. A refractometer comprising:
   a linear scanned array comprising a plurality of photoelectric cells, each cell providing an output pulse during a scan having an amplitude determined by the amount of illumination of the corresponding cell by incident light;
   optical means for directing light onto said array, the particular photoelectric cells of said array which are illuminated by said light being determined by the index of refraction of a sample substance placed in operative association with said optical means, wherein said optical means further acts to receive light reflected by said array and redirect said light reflected by said array back onto said array;
   signal processing means connected to said linear scanned array for receiving and processing cell output pulses to compute the index of refraction of a sample substance placed in operative association with said optical means; and
   a display connected to said signal processing means for reporting a result based on said index of refraction of said sample substance.

2. The refractometer according to claim 1, wherein said optical means includes a reflective surface near said array, said reflective surface having an end portion for receiving only said light reflected by said array.

3. The refractometer according to claim 1, wherein said reflective surface is at an angle of approximately fifteen degrees relative to said array.

4. The refractometer according to claim 1, wherein said optical means includes a prism having a sample surface for receiving said sample substance, and said array extends in a direction substantially parallel to said sample surface.

5. In an automatic refractometer having an array of photoelectric cells and optical means for directing light onto said array, the particular photoelectric cells of said array which are illuminated by said light being determined by the index of refraction of a sample substance placed in operative association with said optical means, the improvement comprising:
   said optical means being configured and arranged with respect to said array to receive light reflected by said array and redirect said light reflected by said array back onto said array.

6. The improvement according to claim 5, wherein said optical means includes a reflective surface near said array, said reflective surface having an end portion for receiving only said light reflected by said array.

7. The improvement according to claim 5, wherein said reflective surface is at an angle of approximately fifteen degrees relative to said array.

8. The improvement according to claim 5, wherein said optical means includes a prism having a sample surface for receiving said sample substance, and said array extends in a direction substantially parallel to said sample surface.

9. A refractometer comprising:
   a housing having a sample well;
   a prism mounted in said housing, said prism having a sample surface facing in an upward direction and accessible through said sample well for receiving a sample substance having a lower index of refraction than said prism;
   means for providing non-parallel light obliquely incident upon a boundary between said sample surface and said sample substance;
   a reflective surface mounted within said housing for receiving light after interaction at said boundary;
   a linear scanned array mounted in said housing, said linear scanned array having a plurality of photoelectric cells facing in a downward direction and receiving light reflected by said reflective surface, each cell providing an output pulse during a scan having an amplitude determined by the amount of illumination of the corresponding cell by incident light;
   signal processing means connected to said linear scanned array for receiving and processing said output pulses to compute the index of refraction of said sample substance; and a display connected to said signal processing means for reporting a result based on said index of refraction of said sample substance.

10. A refractometer comprising:

a linear scanned array comprising a plurality of photo-electric cells, each cell providing an output pulse during a scan having an amplitude determined by the amount of illumination of the corresponding cell by incident light;

a prism having a sample surface for receiving a sample substance having a lower index of refraction than said prism; means for providing non-parallel light obliquely incident upon a boundary between said sample surface and said sample substance;

a reflective surface orientated to define a primary illumination path from said boundary to said linear scanned array via said reflective surface and a secondary illumination path from said linear scanned array back to said linear scanned array via said reflective surface;

signal processing means connected to said linear scanned array for receiving and processing said output pulses to compute the index of refraction of said sample substance; and a display connected to said signal processing means for reporting a result based on said index of refraction of said sample substance.

11. The refractometer according to claim 10, wherein said linear scanned array extends in a direction substantially parallel to said sample surface.

* * * * *